United States Patent
Boersma et al.

(10) Patent No.: US 9,131,871 B2
(45) Date of Patent: Sep. 15, 2015

(54) TABLE HAVING A CENTRAL CELLULAR HONEYCOMB STRUCTURE THERMALLY FUSED IN A SANDWICH CONFIGURATION BETWEEN TWO FIBRE-REINFORCED POLYPROPYLENE FACE SHEETS

(75) Inventors: Walter Boersma, Keyworth Nottinghamshire (GB); Jonathan Richards, Plumtree Nottinghamshire (GB)

(73) Assignee: OMNIA (CS) LIMITED, Nottingham (GB)

( * ) Notice: Subject to any disclaimer, the term of this patent is extended or adjusted under 35 U.S.C. 154(b) by 453 days.

(21) Appl. No.: 13/381,309

(22) PCT Filed: Jun. 30, 2010

(86) PCT No.: PCT/GB2010/051075
§ 371 (c)(1),
(2), (4) Date: Mar. 9, 2012

(87) PCT Pub. No.: WO2011/001174
PCT Pub. Date: Jan. 6, 2011

(65) Prior Publication Data
US 2012/0159711 A1    Jun. 28, 2012

(30) Foreign Application Priority Data

Jun. 30, 2009  (GB) .................................. 0911307.7

(51) Int. Cl.
*A61B 6/04* (2006.01)
*A61B 5/055* (2006.01)

(52) U.S. Cl.
CPC ............. *A61B 5/0555* (2013.01); *A61B 6/0442* (2013.01); *Y10T 156/1034* (2015.01)

(58) Field of Classification Search
CPC .... A61B 6/0407; A61B 6/0442; A61B 5/055; Y10T 156/1034
USPC .......................... 5/601; 128/845; 378/208, 209
See application file for complete search history.

(56) References Cited

U.S. PATENT DOCUMENTS 3,897,345 A * 7/1975 Foster ........................... 378/208
3,947,686 A * 3/1976 Cooper et al. ................ 378/209

(Continued)

FOREIGN PATENT DOCUMENTS

DE          10121130 A1    1/2003
WO      2006086650 A1    8/2006

OTHER PUBLICATIONS

International Search Report issued on Sep. 13, 2010 for International Application No. PCT/GB2010/051075.

*Primary Examiner* — Nicholas Polito
(74) *Attorney, Agent, or Firm* — Knobbe, Martens, Olson & Bear, LLP

(57) ABSTRACT

Magnetic Resonance Imaging (MRI) machine with an integrated medical table top on which a patient can lie is provided. The table top has a central polypropylene cellular honeycomb structure thermally fused in a sandwich configuration between two fiber-reinforced polypropylene face sheets. A strip of fiber-reinforced polypropylene is thermally fused along the entire length of the edge of the sandwich layers and along the end sections of the strip so that the resultant package of layers and end strip is sealingly enclosed to form the tabletop. Table top has a cover which may have a paint or acrylic finish, or may be foamed or "soft-touch" or suitably coated, in order to enhance the patient's comfort and to ensure that tabletop is hard-wearing and readily cleanable.

19 Claims, 3 Drawing Sheets

(56) References Cited

U.S. PATENT DOCUMENTS

| | | | |
|---|---|---|---|
| 4,252,594 A * | 2/1981 | Cooper | 156/285 |
| 4,437,860 A * | 3/1984 | Sigl et al. | 604/385.29 |
| 5,054,049 A * | 10/1991 | Manabe | 378/208 |
| 5,243,639 A * | 9/1993 | Johnson | 378/180 |
| 5,771,513 A * | 6/1998 | Kirchgeorg et al. | 5/625 |
| 5,806,116 A * | 9/1998 | Oliver et al. | 5/621 |
| 7,484,253 B1 * | 2/2009 | Coppens | 5/601 |
| 8,020,227 B2 * | 9/2011 | Dimmer et al. | 5/601 |
| 2006/0185087 A1 * | 8/2006 | Coppens et al. | 5/601 |

* cited by examiner

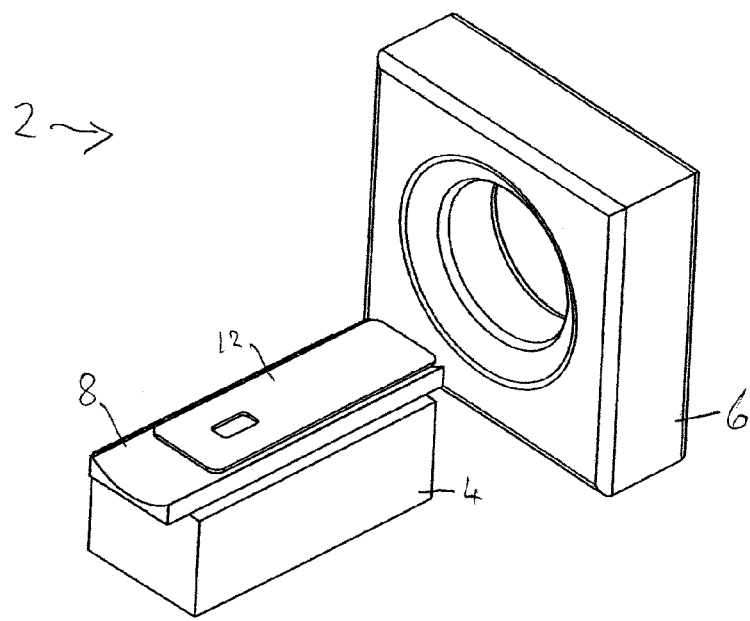
Figure 1
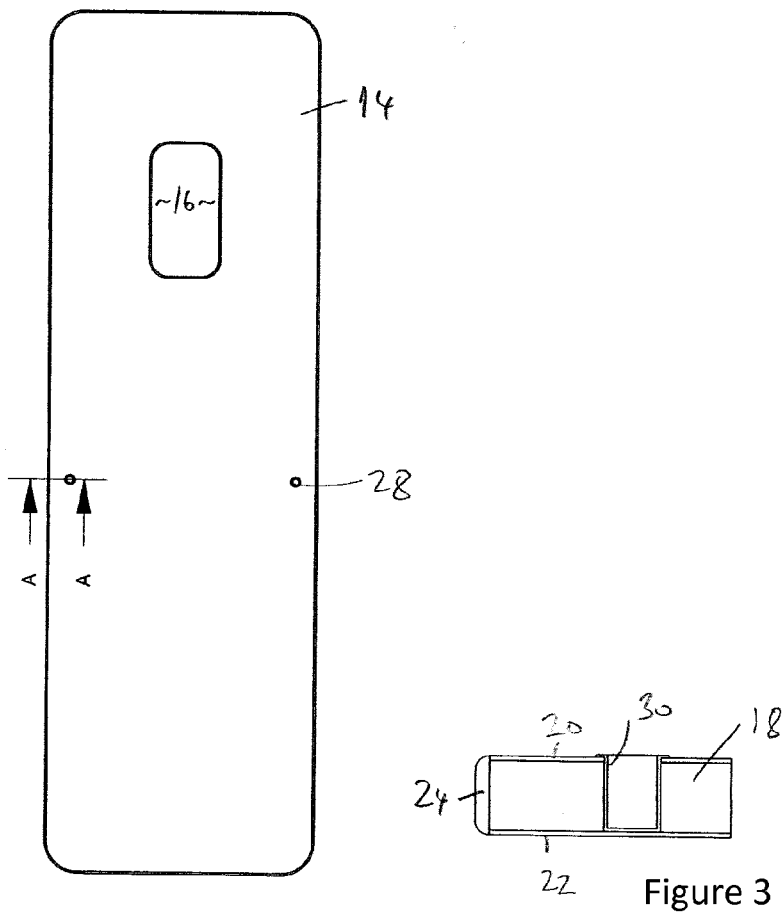
Figure 2
Figure 3

TABLE HAVING A CENTRAL CELLULAR HONEYCOMB STRUCTURE THERMALLY FUSED IN A SANDWICH CONFIGURATION BETWEEN TWO FIBRE-REINFORCED POLYPROPYLENE FACE SHEETS

This application is U.S. National Phase of International Application No. PCT/GB2010/051075, filed Jun. 30, 2010, designating the United States, and published as WO 2011/001174 on Jan. 6, 2011, which claims priority to British Patent Application Nos. 0911307.7, filed Jun. 30, 2009.

FIELD OF THE INVENTION

The present invention relates to a medical treatment table, for example one which may be used with MRI (Magnetic Resonance Imaging) equipment.

BACKGROUND OF THE INVENTION

Advantageously, a medical diagnosis/treatment table has one or more apertures formed in the table, for example in a central region of the table, to allow for cable access or to comfortably accommodate the patient's face when facing downwards, or at side edges of the table to allow for close positioning of additional medical equipment. Also, it may be important to have the facility of anchor points or supports at various places on the table, so that appropriate fixing and positioning to the table base can be provided.

There are a various types of medical treatment tables presently available, for example one type incorporating a carbon fibre body.

However, because of the standard form of construction of a carbon fibre body, any aperture in a carbon fibre body introduces a weakening of the overall structure, and therefore the entire body has to be very carefully designed and precisely manufactured to compensate for any such consequential weakening. Thus, a carbon fibre table must be specifically and individually designed in advance for each particular type of medical analysis or treatment equipment to be used. Modifications to carbon fibre composites are difficult to make and require specialist equipment. Hence adapting the tables to a variety of machines is impractical.

Furthermore, carbon fibre tables cannot readily be used with MRI equipment because the inherent electrical conductivity of the material will tend to have detrimental effects resulting from the enormously large magnet fields generated in MRI equipment during use, causing heating and noise and artifacts on the MRI images. Also, this type of table is not recyclable.

Current MRI tables are made of moulded thermoplastics material. They are curved for comfort as well as for strength, but this means that, in diagnostic procedures requiring accurate positioning, it is not possible to provide accurate matching with images from other machines which have either flat or differently-curved table tops.

Diagnostic table tops are suitable for radiation treatment as well as X-ray diagnostics, but not for MRI diagnostic scans. Thus, the use of various conventional diagnostic equipment for more accurate treatment is limited.

SUMMARY OF THE INVENTION

The present invention provides a medical diagnostic/treatment table comprising a body formed of thermo-composite sandwich layers having a central cellular core thermally fused with and between two polypropylene face sheets, at least one polypropylene strip thermally fused along the edge portion of the sandwich layers to form a sealed enclosure, the table adapted for engagement with medical apparatus for medical diagnosis/treatment of a patient on the table.

In this way, the present invention may provide a table which is light-weight and manoeuvreable, yet very sturdy and robust. Furthermore, the constituent materials are MRI-compatible, low-cost, environmentally-friendly, and recycleable. The structure of the table allows versatile, easy and ready positioning of apertures and anchor points, and a wide range of profiles and contours of table, ensuring that the shape of table can readily be customised to fit with a wide range of medical machines and equipment. Furthermore, the present invention may allow a table to be used with an X-ray machine for locating e.g. a growth, then used with a MRI machine to identify or analyse it more precisely or in additional ways, and then used with a linear accelerator for radio treatment. This use of table and sequence of operations is not possible with conventional tables.

Advantageously, the core comprises a plurality of aligned generally-cylindrical elements with the longitudinal axis orthogonal to the main plane of the face sheets, and preferably a honeycomb structure of cells, and the face sheets are glass fibre reinforced polypropylene.

Preferably, the core comprises a low density thermoplastic foam, such as PET foam with density of 60-200 kg/m3.

A glass fibre reinforced polypropylene strip may be thermally bonded along the entire length of the edge portion of the body and along the end sections of the polypropylene strip, thereby to seal the body and the sandwich layers.

The face sheets may be self reinforced polypropylene.

The table may have a machined aperture extending through the body for accommodating cable access. Furthermore, the table may comprise at least one drilled recess for receiving an insert to hold medical apparatus or positioning aid, the recess accommodating a ring of wear-resistant material.

The body may have a cover which comprises at least one or more of the following: paint coating(s), acrylic coating(s), thermoplastics, two-component "soft-touch" materials, foamed material(s), coating agent(s).

The present invention also provides a method of manufacturing a medical diagnosis/treatment table adapted for engagement with medical apparatus for medical diagnosis/treatment of a patient on the table, the method comprising thermally fusing a body of thermo-composite sandwich layers having a central cellular core between two polypropylene face sheets, then thermally fusing at least one polypropylene strip along the edge portion of the sandwich layers to form a sealed enclosure.

Furthermore, the present invention also provides a method of manufacturing a medical diagnosis/treatment table adapted for engagement with medical apparatus for medical diagnosis/treatment of a patient on the table, the method comprising thermally bonding a body of thermo-composite sandwich layers having a central cellular core between two polypropylene face sheets, then thermally bonding at least one polypropylene strip along the edge portion of the sandwich layers to form a sealed enclosure.

This method may use fibre reinforced thermoplastics, and employ a heat and pressure process to bond the skins on a heat resistant core with hot-melt adhesive (tie layers). This may provide more design freedom, use of foam core materials and incorporate the edges in one stage. It may be preferable to use moulds in this process.

According to another aspect of the present invention, there is provided an edging tool comprising means to supply molten plastics material to a nozzle for applying to a strip of plastics material abutting with a configuration of a central cellular core sandwiched between two face sheets, thereby to form a sealing engagement between the strip and the sandwich configuration.

According to another aspect of the present invention, there is provided an edging tool comprising means to supply molten plastics material to a nozzle for applying to a strip of plastics material abutting with a configuration of a central cellular core sandwiched between two face sheets, thereby to form a sealing engagement between the strip and the sandwich configuration.

Preferably the tool comprises two nozzles for applying molten plastics material to respective edges of the plastics material strip.

According to this aspect of the present invention, there is also provided a method of manufacturing a medical diagnosis/treatment table adapted for engagement with medical apparatus for medical diagnosis/treatment of a patient on the table, the method comprising supplying molten plastics material to a nozzle for applying to a strip of plastics material abutting with a configuration of a central cellular core sandwiched between two face sheets, thereby to form a sealing engagement between the strip and the sandwich configuration.

Preferably, the method comprises applying molten plastics material to each of the two respective edges of the strip of plastics material.

Advantages of the Present Invention

An advantage of the present invention is optimising the manufacture of the table in terms of speed, energy consumption as well as reducing the quantity of components and materials required.

A further advantage is the optimisation of materials cost and the provision of a technically advantageous and economical alternative to existing technologies and best practice.

A further advantage of the present invention is to provide a system that significantly increases the recyclability of the materials used, whether in this industry or for an alternative use.

A further advantage is that the present invention allows a table of the invention to be used on both MRI and X-ray machines as appropriate, thereby offering the opportunity of a patient to remain on the table for successive diagnosis and treatment. Also, a single type of table can be used for a wide variety of machines, offering the possibility of bulk-buying of such tables and hence the opportunity of cost savings.

The materials used can be specified to have high tensile structural properties and recyclability, light weight and resistance to corrosion, as well as having good load fatigue and absorption properties. Such materials are plastics or composite materials such as as fibre-reinforced polymer (FRP) or glass-reinforced plastic (GRP). One suitable material is MonoPan™ a woven glass and polypropylene faced panel with polypropylene honeycomb supplied by Omnia (CS) Ltd.

Other materials combinations of particular interest and relevence for X_Ray imaging are PET foam core, giving a homogeneous density distribution and self-reinforced PP skins (Brand: Curv), with very low density, and PET or PBT skins e.g. with fibre reinforcement. These materials can be joined using heat activated adhesive films (hot-melt).

Furthermore, the method of manufacturing the table reduces assembly time by fully utilising the unique properties of thermoplastic panel.

The present invention utilises a thermo fusion technique, such as plastic extrusion welding or hot air welding with a simple hand held tool technique.

This method of assembly and joining creates a structure that is impervious to moisture ingress as it is "sealed" from the inside due to the plastic welding with the external "capping" providing an aesthetic and protective barrier.

The term "fusing" includes welding operations whereby the polypropylene molecules mix in a liquid state to form a connection therebetween of similar strength to continuous material without the connection.

The term "thermal bonding" includes operations involving the use of adhesives and other similar materials

APPLICATIONS OF THE PRESENT INVENTION

The present invention relates to a medical diagnosis/treatment table which may include appropriate base, supports and/or legs, and equally to a table top alone for engagement with and/or adapted for mounting on a conventional support or base. Likewise, a table of the present invention may be integral with and/or form part of a medical diagnosis/treatment machine or equipment, or may engage with or be adapted for engagement with such a machine or equipment.

The present invention is particularly suited to MRI machines for analysis and/or treatment of patients, and also X-ray machines, but is also applicable to other medical equipment and machinery.

BRIEF DESCRIPTION OF THE DRAWINGS

In order that the invention may more readily understood, a description is now given, by way of example only, reference being made to various embodiments of the present invention, in which:—

FIG. 1 is perspective view of a Magnetic Resonance Imaging machine and table embodying the present invention;

FIG. 2 is plan view of the table top of FIG. 1;

FIG. 3 is a section through the table top of FIG. 2 along the lines A-A;

DETAILED DESCRIPTION OF THE DRAWINGS

Figure 4:
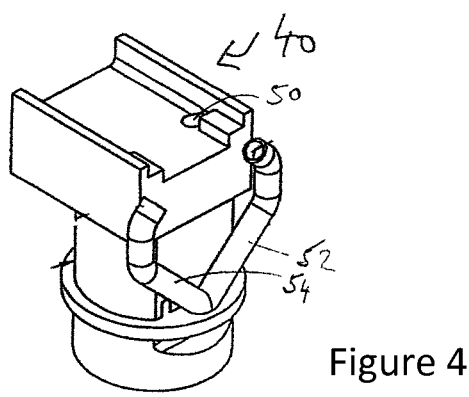
FIG. 4 is a perspective view of an edging tool for the manufacture of the table top of FIG. 1.

There is illustrated in FIGS. 1 to 3 a Magnetic Resonance Imaging (MRI) machine with a table for a patient undergoing diagnosis and/or treatment embodying the present invention, comprising an MRI machine 2 with a table plinth 4 and magnet coils 6, the plinth 4 and table 8 being movable to coils 6 until table 8 (and a table top 12 of the present invention on which a patient may lie) is wholly enclosed within the coils.

Table top 12 is shown in greater detail in FIGS. 2 and 3, having an upper surface 14 on which a patient can lie, and containing an aperture 16 to accommodate cable access.

Table top 12 has a central polypropylene cellular honeycomb structure 18 of thickness 25 mm for high stiffness (but in applications where thickness is critical and stiffness is less important, then the thickness may be reduced to about 17 mm, and the maximum extremes ranging being between 12 and 30 mm) which is thermally fused in a sandwich configuration between two glass fibre-reinforced polypropylene face sheets 20, 22 of thickness 1 mm (alternatively in the range 0.5 to 1.4 mm, preferably 0.65 to 1.00 mm), and core density 80 kg/m$^3$ (alternatively in the range 80 to 120 kg/m$^3$).

A strip 24 of glass fibre-reinforced polypropylene of width 26.75 mm, about 4 mm less than the thickness of all the sandwich layers, is thermally fused along the entire length of the edge of the sandwich layers and along the end sections of the strip so that the resultant package of layers and end strip is sealingly enclosed to form the table top 14.

Table top 14 has a cover (not shown) which may have a paint or acrylic finish, or may be foamed or "soft-touch" or suitably coated, in order to enhance the patient's comfort and to ensure that table top 14 is hard-wearing and readily cleanable.

Table top 14 has a number of recesses 28 which are available to act as anchor points, for example for particular medical equipment (e.g. drip-feed equipment) or for securing temporarily the table at a particular location or relative to the associated MRI machine. The recesses 28 are filled with closely-fitting plugs when use of the anchor points is not required. The structure of the table of the present invention ensures that such anchor points can easily and quickly be provided, merely by suitably drilling the completed table in the places where anchor points are required. This is in stark contrast with the situation with carbon fibre tables, wherein the positioning of anchor points is severely limited, as they can only occur in specific places being dependent on the overall strength profile and characteristics of the table, otherwise the structure could be significantly weakened.

Clearly, even more important in prior art carbon fibre tables is where to position any aperture which is equivalent to that of aperture 16 for table top 14 of the present invention.

It can be really difficult, if not impossible, to incorporate such an aperture in conventional tables, without seriously jeopardising the strength of the table. However, in the present invention, aperture 16 is provided with no difficulty at all.

Each recess 28 has a ring 30 of wear-resistant plastics material for example hard-wearing plastics materials (including for example engineering plastics materials including those marketed under the trademark DELRIN) which is securely and permanently held (e.g. by being previously bonded or glued in an appropriately sized hole drilled in the sandwich layers), in order to ensure easy, secure and long-lasting anchoring.

FIG. 4 shows an edging tool 40 which is used to form a sealing engagement of polypropylene strip 24 along the entire length of the edge of the composite sandwich configuration of honeycomb structure 18 and face sheets 20, 22. Polypropylene is heated in a reservoir 42 and then, in a molten form, is pumped along pipes 44 and 46 to respective nozzle outlets 48, 50 where it is applied onto a section of strip 24 positioned to contact with a respective part of the composite honeycomb structure 18 and face sheets 20, 22, thereby causing a thermal bonding between those parts, the edging tool being passed along the length of the edge of the sandwich until the entire edge is sealed.

There are also pipes 52, 54 to provide a heated air flow in order to pre-heat the section of strip 24 as it approaches the point of thermal fusion with the molten polypropylene coming out of outlets 48, 50.

Figure 5:
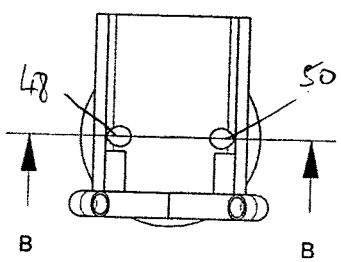
FIG. 5 is a plan view of the edging tool of FIG. 4.
Figure 6:
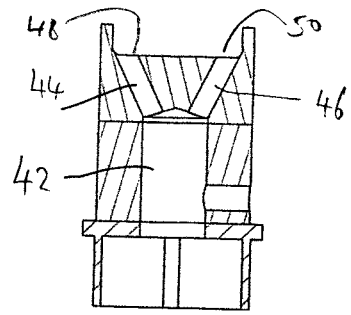
FIG. 6 is a section view along the lines B-B of FIG. 5.
Figure 7:
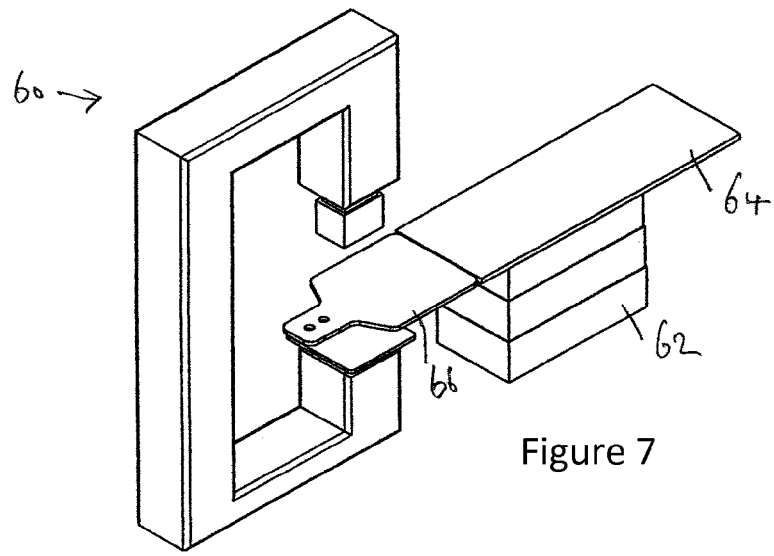
FIG. 7 is a perspective of an X-ray machine and table of a second embodiment of the present invention.
Figure 8:
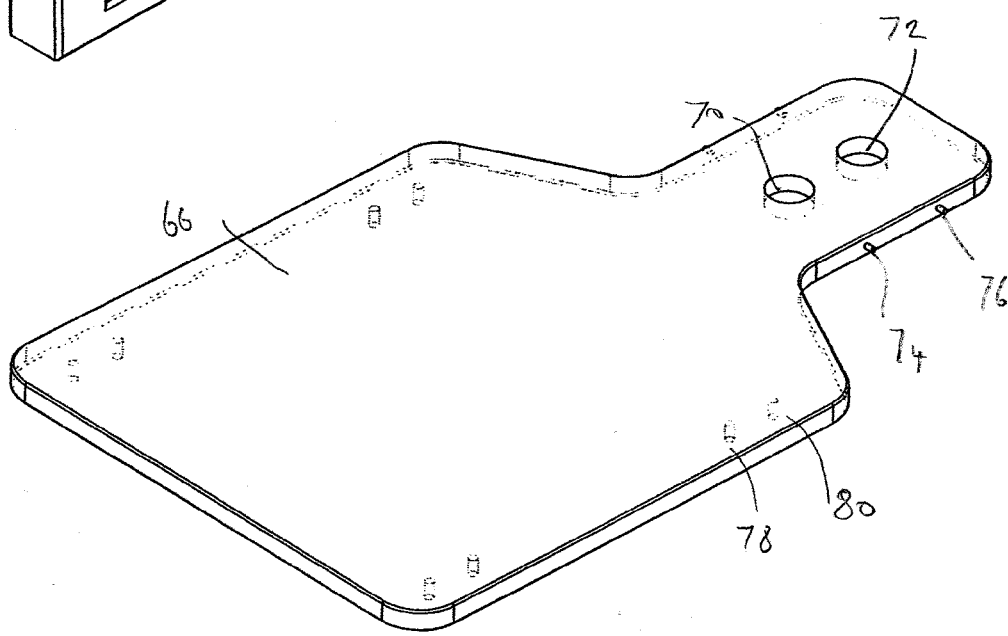
FIG. 8 is a perspective view of a detail of the table of FIG. 7.

FIGS. 5 and 6 shows a second embodiment of the present invention comprising a diagnostic X-ray machine 60 having a moveable table plinth 62 and table 64 on which a patient can lie, for movement to a position in which table end section 66 embodying the present invention (and hence a patient laying thereon) is exposed to the X-rays emitted from X-ray gun 68.

The table section 66 of this second embodiment has features equivalent to the first embodiment, and is manufactured in similar fashion. In a variant, all of table 64 embodies the present invention.

Table end section 66 is planar with two closely adjacent apertures 70, 72 for cable access and located in a peninsula region 74 having two laterally extending protrusions 74, 76 fixing a head rest. Table end section 66 has four pairs of holes 78, 80 which are for fixing points.

What is claimed is:

1. A medical diagnosis/treatment table comprising a body formed of polypropylene sandwich layers having a central cellular core thermally welded to and between two polypropylene face sheets whereby polypropylene molecules of the core and the face sheets have been mixed in a liquid state to form a connection therebetween of similar strength to continuous material without the connection, and at least one polypropylene strip thermally welded along the edge portion of the sandwich layers whereby polypropylene molecules of the at least one strip and the edge portion of the sandwich layers have been mixed in a liquid state to form a connection therebetween of similar strength to continuous material without the connection, wherein the face sheets and the at least one strip form a sealed enclosure, the body adapted for engagement with medical apparatus for medical diagnosis/treatment of a patient on the table;

wherein the at least one polypropylene strip is thermally welded along the edge portion of the sandwich layers by a process comprising:

heating polypropylene into a molten form; and applying the molten form of polypropylene onto a section of the strip positioned to contact with a respective part of the core and the two polypropylene face sheets, thereby causing a thermal bonding therebetween.

2. The table as in claim 1 wherein the core comprises a plurality of aligned generally-cylindrical elements with a longitudinal axis orthogonal to the main plane of the face sheets.

3. The table as in claim 1 wherein the core comprises a honeycomb structure of cells.

4. The table as in claim 1 wherein the face sheets are glass fibre reinforced polypropylene.

5. The table as in claim 4 further comprising a glass fibre reinforced polypropylene strip thermally welded along the entire length of the edge portion of the body and along the end sections of the polypropylene strip whereby polypropylene molecules of the glass fibre reinforced polypropylene strip and the edge portion of the body and the end sections of the polypropylene strip have been mixed in a liquid state to form a connection therebetween of similar strength to continuous material without the connection, thereby to seal the body and the sandwich layers.

6. The table as in claim 1 wherein the face sheets are self reinforced polypropylene.

7. The table as in claim 1 wherein the table comprises a machined aperture extending through the body for cable access.

8. The table as in claim 1 further comprising at least one machined recess for receiving an insert to hold medical apparatus.

9. The table as in claim 8 wherein the recess accommodates a ring of wear-resistant material.

10. The table as in claim 1 wherein the body has a cover which comprises at least one or more selected from the group consisting of: paint coating(s), acrylic coating(s), thermoplastics, two-pack component materials, foamed material(s), and coating agent(s).

11. A method of manufacturing a medical diagnosis/treatment table adapted for engagement with medical apparatus for medical diagnosis/treatment of a patient on the table, the method comprising:

thermally welding a body of polypropylene sandwich layers having a central cellular core between two polypropylene face sheets whereby polypropylene molecules of the core and the face sheets are mixed in a liquid state to form a connection therebetween of similar strength to continuous material without the connection, and then thermally welding at least one polypropylene strip along the edge portion of the sandwich layers by a process comprising heating polypropylene into a molten form; and applying the molten form of polypropylene onto a section of the strip positioned to contact with a respective part of the core and the two polypropylene face sheets, thereby causing a thermal bonding therebetween, whereby polypropylene molecules of the polypropylene strip and the edge portion of the sandwich layers are mixed in a liquid state to form a connection threrebetween of similar strength to continuous material without the connection wherein the face sheets and the at least one strip form a sealed enclosure.

12. The method as in claim 11 wherein the core comprises a plurality of aligned generally-cylindrical elements with the longitudinal axis orthogonal to the main plane of the face sheets.

13. The method as in claim 11 wherein the core comprises a honeycomb structure of cells.

14. The method as in claim 11 wherein the face sheets are glass fibre reinforced polypropylene.

15. The method as in claim 14 comprising thermally welding a glass fibre reinforced polypropylene strip along the entire length of the edge portion of the body and along the end sections of the polypropylene strip whereby polypropylene molecules of the glass fibre reinforced polypropylene strip and the edge portion of the body and the end sections of the polypropylene strip are mixed in a liquid state to form a connection therebetween of similar strength to continuous material without the connection, thereby to seal the body and the sandwich layers.

16. The method as in claim 11 further comprising machining an aperture extending through the body for cable access.

17. The method as in claim 11 further comprising machining at least one recess for receiving an insert to hold medical apparatus.

18. The method as in claim 11 further comprising machining a recess to accommodate a ring of wear-resistant material.

19. The method as in claim 11 further comprising providing a cover which comprises at least one or more of the following: paint coating(s), acrylic coating(s), thermoplastics, two-pack component materials, foamed material(s), coating agent(s).

* * * * *